US010532187B2

(12) United States Patent
Schultz et al.

(10) Patent No.: US 10,532,187 B2
(45) Date of Patent: Jan. 14, 2020

(54) REUSABLE CATHETER HANDLE SYSTEM

(71) Applicant: Biosense Webster (Israel) Ltd., Yokneam (IL)

(72) Inventors: Jeffrey Schultz, Chino, CA (US); Corey Rousu, Glendale, CA (US); Daniele Ghidoli, Irwindale, CA (US); Simon Jung, Placentia, CA (US); Jeffrey Clark, Castaic, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 176 days.

(21) Appl. No.: 15/786,414

(22) Filed: Oct. 17, 2017

(65) Prior Publication Data

US 2019/0111238 A1 Apr. 18, 2019

(51) Int. Cl.
*A61M 25/01* (2006.01)
*A61B 17/12* (2006.01)

(52) U.S. Cl.
CPC .... *A61M 25/0136* (2013.01); *A61M 25/0147* (2013.01); *A61B 2017/12054* (2013.01)

(58) Field of Classification Search
CPC .......... A61M 25/0133; A61M 25/0136; A61M 25/0144; A61M 25/0147; A61M 2025/0161; A61M 2025/0163
See application file for complete search history.

(56) References Cited

U.S. PATENT DOCUMENTS 5,254,088 A * 10/1993 Lundquist ......... A61M 25/0144
600/585
5,391,199 A 2/1995 Ben-Haim
5,441,483 A * 8/1995 Avitall ............... A61B 18/1492
604/95.05
5,456,664 A 10/1995 Heinzelman et al.
(Continued)

FOREIGN PATENT DOCUMENTS

WO 94/06349 3/1994
WO 96/05768 2/1996
WO 97/24981 7/1997

OTHER PUBLICATIONS

U.S. Appl. No. 12/346,834, filed Dec. 30, 2008, titled "Deflectable Sheath Introducer".

(Continued)

*Primary Examiner* — Quynh-Nhu H. Vu
(74) *Attorney, Agent, or Firm* — Dergosits & Noah LLP; Todd A. Noah

(57) ABSTRACT

A steerable catheter is disclosed, having an elongated, tubular catheter body with at least one deflection member slidably disposed within a lumen, secured at a distal end to a tip section and terminating in an interconnect at a proximal end and a handle releasably attached to the proximal end of the catheter body. The handle has at least one sliding member coupled to an actuator, such that manipulation of the actuator causes relative longitudinal movement with respect to the handle, wherein the interconnect and the sliding member engage when the handle is attached to the catheter body so that the relative longitudinal movement of the sliding member is transmitted to the deflection member and wherein the interconnect and the sliding member disengage when the handle is released from the catheter body.

21 Claims, 4 Drawing Sheets

(56) References Cited

U.S. PATENT DOCUMENTS

| | | | |
|---|---|---|---|
| 5,471,982 A | 12/1995 | Edwards et al. | |
| 5,718,241 A | 2/1998 | Ben-Haim et al. | |
| 5,769,858 A | 6/1998 | Pearson et al. | |
| 6,007,531 A | 12/1999 | Snoke et al. | |
| 6,013,052 A * | 1/2000 | Durman | A61B 18/1492 604/264 |
| 6,066,125 A * | 5/2000 | Webster, Jr. | A61B 5/015 604/528 |
| 6,156,027 A * | 12/2000 | West | A61M 25/0136 600/585 |
| 6,171,277 B1 | 1/2001 | Ponzi | |
| 6,200,315 B1 * | 3/2001 | Gaiser | A61B 18/1492 606/41 |
| 6,221,070 B1 | 4/2001 | Tu et al. | |
| 6,226,542 B1 | 5/2001 | Reisfeld | |
| 6,301,496 B1 | 10/2001 | Reisfeld | |
| 6,892,091 B1 | 5/2005 | Ben-Haim et al. | |
| 7,027,851 B2 * | 4/2006 | Mejia | A61B 5/0422 600/374 |
| 7,039,450 B2 * | 5/2006 | Duarte | A61B 5/0422 600/374 |
| 8,133,224 B2 | 3/2012 | Geiselhart | |
| 8,137,308 B2 | 3/2012 | Schultz | |
| 8,257,386 B2 | 9/2012 | Lee et al. | |
| 8,348,888 B2 | 1/2013 | Selkee | |
| 8,628,545 B2 | 1/2014 | Cabrera et al. | |
| 8,636,752 B2 | 1/2014 | Cabrera et al. | |
| 8,777,889 B2 * | 7/2014 | Joshi | A61B 17/3478 604/181 |
| 8,777,898 B2 | 7/2014 | Suon et al. | |
| 8,795,275 B2 | 8/2014 | Hafner | |
| 8,808,345 B2 | 8/2014 | Clark et al. | |
| 9,339,173 B2 | 5/2016 | McWeeney et al. | |
| 9,539,413 B2 * | 1/2017 | Ogle | A61M 25/0136 |
| 9,566,048 B1 | 2/2017 | Knodel et al. | |
| 9,629,982 B2 * | 4/2017 | Caples | A61B 18/1492 |
| 2003/0028182 A1 | 2/2003 | Abboud et al. | |
| 2009/0137953 A1 * | 5/2009 | Fischer | A61M 25/0136 604/95.04 |
| 2010/0164137 A1 * | 7/2010 | Selkee | A61M 25/0136 264/242 |
| 2012/0197190 A1 | 8/2012 | Suon et al. | |
| 2014/0249473 A1 | 9/2014 | Suehara | |
| 2014/0331818 A1 | 11/2014 | Kupferschmid | |
| 2016/0095650 A1 | 4/2016 | Greifeneder et al. | |
| 2017/0326337 A1 * | 11/2017 | Romoscanu | A61M 25/0136 |

OTHER PUBLICATIONS

International Search Report and Written Opinion for International Application No. PCT/US201/0055128; dated Feb. 2, 2019.

* cited by examiner

REUSABLE CATHETER HANDLE SYSTEM

FIELD OF THE PRESENT DISCLOSURE

This invention relates to a catheter having a reusable control handle and a steerable disposable catheter body.

BACKGROUND

Medical catheterizations are routinely carried for many procedures. In one representative example, cardiac arrhythmias including atrial fibrillation may be diagnosed as well as treated by employing a variety of catheters to access the patient's heart in a minimally invasive manner. Diagnosing such conditions may involve mapping the cardiac tissue to locate aberrant electrical pathways and currents within the heart, as well as to determine mechanical and other aspects of cardiac activity. Various methods and devices have been described for mapping the heart. Such methods and devices are described, for example, in U.S. Pat. Nos. 5,471,982, 5,391,199 and 5,718,241 and in PCT patent publications WO94/06349, WO96/05768 and WO97/24981. Further, one or more catheters may also be employed to deliver energy to desired locations within the patient's anatomy to pace the heart or to ablate tissue and form nonconductive lesions that may block or modify the propagation of unwanted electrical signals from their origin to help restore more normal function. As will be appreciated, these examples are for the purposes of illustration only, as a wide variety of other procedures may be facilitated through use of suitable catheterization techniques. Typically, the ability to control the exact position and orientation of the catheter tip is critical and largely determines how useful the catheter is.

To that end, directional catheters have been designed to be deflectable, such as by manipulation of a puller wire or other deflection member disposed within an off-axis lumen and attached to a distal location of the catheter. Correspondingly, applying tension to the puller wire causes the tip of the catheter to deflect. Various designs exist, including unidirectional catheters that employ a single puller wire and bi-directional catheters that may have two puller wires extending within opposing off-axis lumens. More complex designs featuring a greater number of puller wires are also possible. Such catheters typically have a control handle at their distal end which have a thumb knob, a rotatable grip or other actuation mechanism that is manipulated by an electrophysiologist to position a distal end of the catheter at the desired location and/or operate electrode assemblies, such as contraction, expansion, deployment, retraction, etc.

As with all medical equipment, prevention of iatrogenic conditions is of paramount concern. Ensuring sterility of the catheter may help minimize the risk of transmitting infectious agents. One strategy involves using new equipment with each procedure. With more complex equipment, such as the catheters of this disclosure, this may represent a significant cost. To address this concern, the equipment may be cleaned and sterilized before the next use. However, costs and delays are associated with this strategy as well, particularly due to the difficulties involved with cleaning the elongated catheter shaft which typically has multiple lumens. Accordingly, it would be desirable to provide a catheter system that reduces these drawbacks by employing a reusable handle mechanism that may be readily sterilized for use with a disposable catheter body, particularly in light of the observation that the handle represent a significant fraction of the overall cost. Similarly, it would be desirable to provide a catheter system having a detachable connection between the reusable handle and the disposable shaft that couples the actuation mechanisms of the handle with components of the catheter shaft, such as puller wires, that control deflection of the catheter tip. The techniques of this disclosure as described in the following materials satisfy these and other needs.

SUMMARY

The present disclosure is directed to a steerable catheter with an elongated, tubular catheter body having a proximal end and a tip section at a distal end, and at least one lumen extending therethrough. At least one deflection member may be slidably disposed within the lumen, secured at a distal end to the tip section and terminating in an interconnect at the proximal end. A handle is configured to be releasably attached to the proximal end of the catheter body, having at least one actuator and at least one sliding member associated with the handle and coupled to the actuator, such that manipulation of the actuator causes relative longitudinal movement with respect to the handle. The interconnect and the sliding member engage when the handle is attached to the catheter body so that the relative longitudinal movement of the sliding member is transmitted to the deflection member and wherein the interconnect and the sliding member disengage when the handle is released from the catheter body.

In one aspect, the actuator comprises a rotating member coupled to the sliding member by a pin traveling within a camming slot of the rotating member.

In one aspect, the catheter body may have at least two lumens extending therethrough, with two deflection members, each slidably disposed within respective lumens, both secured at a distal end to the tip section and terminating in interconnects at the proximal ends, and the actuator may be coupled to the two sliding members, wherein each interconnect and each sliding member engage when the handle is attached to the catheter body so that the relative longitudinal movement of each sliding member is transmitted to each engaged deflection member and wherein each interconnect and each sliding member disengage when the handle is released from the catheter body. Correspondingly, the actuator may be a rotating member coupled to each sliding member by pins traveling within respective camming slots of the rotating member so that rotation of the actuator in a first direction causes movement of one sliding member in a relatively distal direction and movement of the other sliding member in a relatively proximal direction, while rotation of the actuator in a second direction causes movement of the one sliding member in a relatively proximal direction and movement of the other sliding member in a relatively distal direction.

In one aspect, the camming slot of the actuator may have a radius that displaces the sliding member at a same ratio of rotation to movement over a range of travel of the actuator.

In one aspect, the engagement of the sliding member and the interconnect may involve a projection fitting within a recess. A ramp on one of the sliding member and the interconnect may deflect the projection until positioned coextensively with the recess.

In one aspect, the sliding member may travel within a guide formed in a distal portion of the handle.

In one aspect, the catheter body may be attached to the handle by a threaded housing.

In one aspect, the interconnect may be stabilized with respect to the catheter body prior to attachment to the handle by a frangible support. The frangible support may be configured to break following manipulation of the actuator by a user.

In one aspect, electronic circuitry may be integrated into at least one of the catheter body and the handle such that the electronic circuitry is in communication with components in the catheter body when the handle is attached to the catheter body.

This disclosure also includes a handle for a steerable catheter having a coupling for attaching a proximal end of a catheter body, at least one actuator and at least one sliding member associated with the handle and coupled to the actuator, such that manipulation of the actuator causes relative longitudinal movement with respect to the handle. The catheter body to be releasably attached to the handle has at least one deflection member slidably disposed within a lumen, secured at a distal end to a tip section and terminating in an interconnect at the proximal end. The sliding member may be configured to engage with the interconnect when the handle is attached to the catheter body so that the relative longitudinal movement of the sliding member is transmitted to the deflection member and the sliding member may be configured to disengage from the interconnect when the handle is released from the catheter body.

In one aspect, the actuator may have a rotating member coupled to the sliding member by a pin traveling within a camming slot of the rotating member.

In one aspect, the catheter body may have at least two lumens extending therethrough, with two deflection members, each slidably disposed within respective lumens, both secured at a distal end to the tip section and terminating in interconnects at the proximal ends, and wherein the actuator is coupled to two sliding members, wherein each sliding member is configured to engage with each interconnect when the handle is attached to the catheter body so that the relative longitudinal movement of each sliding member is transmitted to each engaged deflection member and wherein each sliding member is configured to disengage from each interconnect when the handle is released from the catheter body. The actuator may have a rotating member coupled to each sliding member by pins traveling within respective camming slots of the rotating member so that rotation of the actuator in a first direction causes movement of one sliding member in a relatively distal direction and movement of the other sliding member in a relatively proximal direction, while rotation of the actuator in a second direction causes movement of the one sliding member in a relatively proximal direction and movement of the other sliding member in a relatively distal direction.

In one aspect, the camming slot of the actuator may have a radius that displaces the sliding member at a same ratio of rotation to movement over a range of travel of the actuator.

In one aspect, the sliding member may be configured to engage the interconnect by a projection fitting within a recess.

In one aspect, the sliding member may travel within a guide formed in a distal portion of the handle.

In one aspect, electronic circuitry may be integrated into the catheter body such that the electronic circuitry is in communication with components in the catheter body when the handle is attached to the catheter body.

This disclosure also includes an elongated, tubular catheter body having a proximal end and a tip section at a distal end, at least one lumen extending therethrough and at least one deflection member slidably disposed within the lumen, secured at a distal end to the tip section and terminating in an interconnect at the proximal end. The proximal end of the catheter body may be configured to be releasably attached to a handle having at least one sliding member, wherein the interconnect and the sliding member engage when the handle is attached to the catheter body so that the relative longitudinal movement of the sliding member is transmitted to the deflection member and wherein the interconnect and the sliding member disengage when the handle is released from the catheter body.

In one aspect, the interconnect may be stabilized with respect to the catheter body prior to attachment to the handle by a frangible support.

In one aspect, electronic circuitry may be integrated into the catheter body such that the electronic circuitry is in communication with the handle when the handle is attached to the catheter body.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a," "an" and "the" include plural referents unless the content clearly dictates otherwise.

Figure 1:
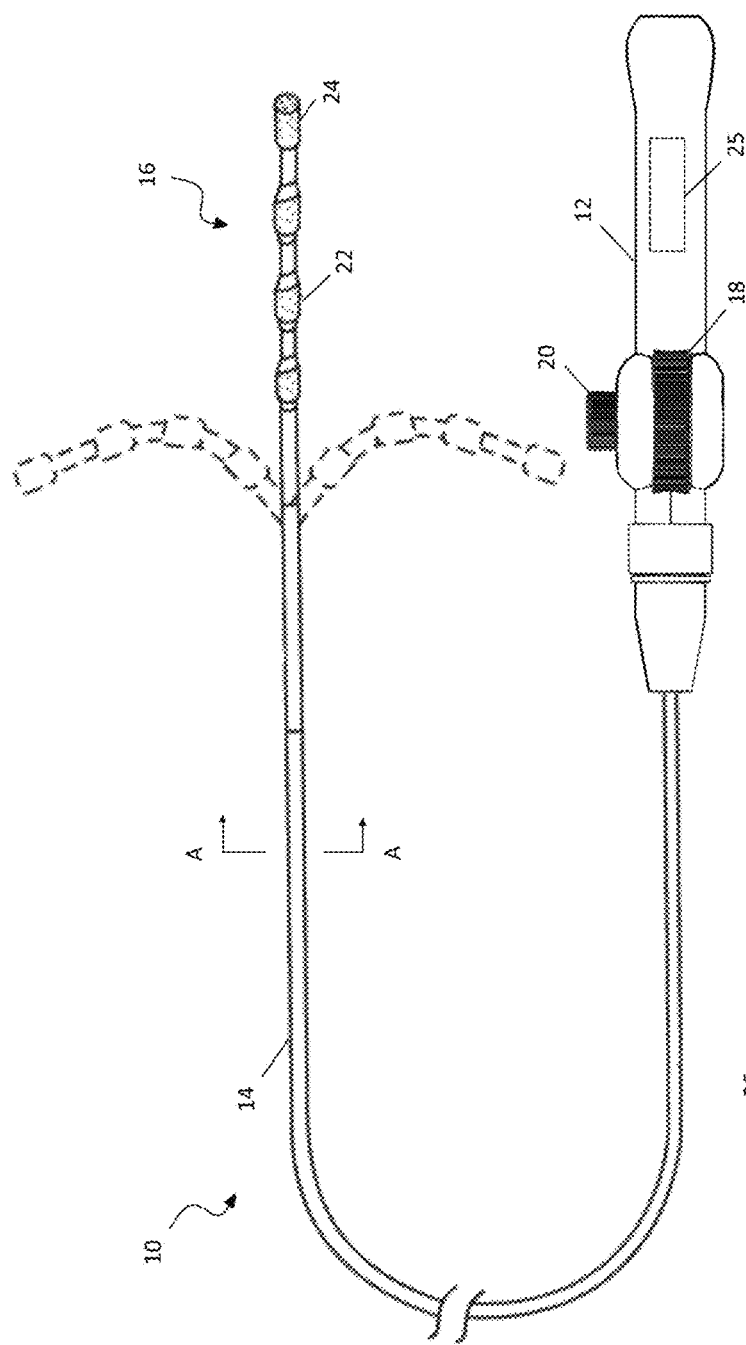
FIG. 1 is a schematic elevational view of a catheter system having a reusable handle and a disposable catheter body, according to one embodiment.

To help illustrate aspects of this disclosure, FIG. 1 schematically depicts a steerable catheter system 10 having a reusable handle 12 and a disposable elongated body 14 that may be attached and detached from the handle. The catheter body 14 generally comprises an elongated tubular construction and may have an axial or central lumen. The catheter body 14 is flexible, i.e., bendable, but substantially non-compressible along its length. The catheter body 12 can be of any suitable construction and made of any suitable material. In one embodiment, an outer wall may be made of polyurethane or PEBAX. The outer wall may also include an imbedded braided mesh of stainless steel or the like to increase torsional stiffness of the catheter body 14 so that when the handle 12 is rotated, a tip section 16 will rotate in a corresponding manner. The outer diameter of the catheter body 14 is not critical, and will vary depending on the intended application of the catheter. As a representative example, the diameter may be about 8 french or less. Likewise, the thickness of the outer wall is not critical, but is thin enough so that the catheter body 14 can accommodate deflection members (e.g., puller wires), lead wires, and any other desired wires, cables or tubings while maintaining the desired outer diameter. As warranted, the inner surface of the outer wall may be lined with a stiffening tube to provide improved torsional stability. For purposes of illustration only, the outer wall may have an outer diameter of from about 0.090 inch to about 0.94 inch and an inner diameter of from about 0.061 inch to about 0.065 inch. Likewise, the overall length of catheter system 10 may vary depending on the intended application, and may be about 48 inches in some embodiments.

Handle 12 and its components may be formed from suitable metals and/or polymeric materials and has an actuator 18 configured as a rotating member, taking the form of a thumb wheel in this embodiment, that actuates one or more deflection members, such as puller wires as described in further detail below. The control handle may also include a tension knob 20 that enables the user to adjust the ease by which the actuator 18 can be rotated, or may lock actuator 18 in a desired position. Manipulation of actuator 18 may impart a desired degree of deflection in tip section 16, which may be bi-directional as indicated in the figure. In other embodiments, uni-directional or other types of deflection may be employed. Although a thumb wheel actuator is depicted in this embodiment, it will be appreciated that any suitable actuator design may be employed as desired, including sliders, pistons, rocker handles or the like. Exemplary details of deflection assemblies and control handles are described in co-pending U.S. application Ser. No. 12/346, 834, filed Dec. 30, 2008, entitled DEFLECTABLE SHEATH INTRODUCER, and commonly-owned U.S. Pat. No. 8,137,308, issued Mar. 20, 2012, entitled CATHETER WITH ADJUSTABLE DEFLECTION SENSITIVITY and U.S. Pat. No. 8,348,888, issued Jan. 8, 2013, entitled STEERING MECHANISM FOR BI-DIRECTIONAL CATHETER, the entire disclosures of each are hereby incorporated by reference.

In the depicted embodiment, catheter system 10 is configured for use in a electrophysiologic (EP) procedure, such as for mapping, pacing and/or ablation in the heart. As such, distal tip section 16 may have multiple electrodes, including ring electrodes 22 and tip electrode 24, which may be irrigated if desired as depicted. Ring electrodes 22 may range in length from about 1 mm to about 3 mm, and may be spaced apart in any fashion as desired so long as their edges do not touch. As will be appreciated, the electrodes may be used for mapping, pacing, ablation or other operations and may be perforated to deliver irrigation fluid for controlling tissue temperature during the procedure. Handle 12 may incorporate a printed circuit board (PCB) 25 (shown in phantom in FIG. 1) or equivalent circuitry to be used in conjunction with controlling, receiving and/or delivering signals to the electrodes in the distal tip section 16 or any other components, such as location sensors, thermocouples or the like. For example, PCB 25 may include a microprocessor for storing or preprocessing data measured by the electrodes to facilitate communication with a patient interface unit or other similar equipment. However, these and other aspects associated with EP catheters are intended as illustrations only and the techniques of this disclosure for providing a reusable handle with a steerable, disposable catheter body are relevant for any catheter that may be used in any procedure for which steerability is desirable.

Figure 2:
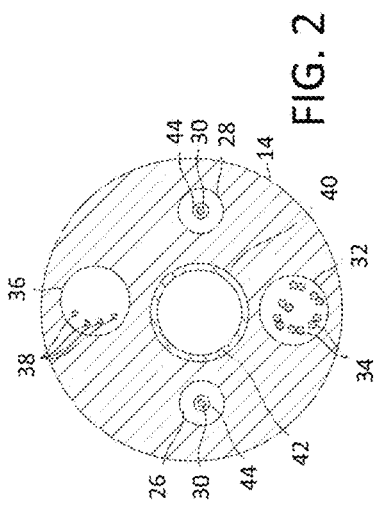
FIG. 2 is a cross section view of the catheter body of FIG. 1, according to one embodiment.

A cross section of catheter body 14, taken at A-A, is shown in FIG. 2. In this embodiment, two off-axis lumens 26 and 28 accommodate puller wires 30, which are slidable within the lumens so that manipulation of actuator 18 may be used to deflect tip section 16. Catheter body 14 may have additional lumens as warranted by the intended application. For example, lumen 32 may carry lead wires and thermocouple wires 34 for communicating electrical signals to and from ring electrodes 22 and tip electrode 24. Further, lumen 36 may carry location sensor cables 38, used in conjunction with a positioning system, such as the CARTO® 3 System embodying methods as disclosed in U.S. Pat. Nos. 6,226, 542, and 6,301,496, and 6,892,091, available from Biosense Webster, Inc. (Diamond Bar, Calif.), while lumen 40 may carry irrigation tubing 42. Each puller wire 30 is made of any suitable metal, such as stainless steel or Nitinol, or other appropriate material, and may have a coating or sleeve 44 of Teflon® or the like. Each puller wire 30 may have a diameter ranging from about 0.006 inch to about 0.0010 inch. The puller wires 30 may be secured at a desired location in tip section 16, such as by welding to tip electrode 24 or through an anchor embedded in the material of the catheter body.

Figure 3:
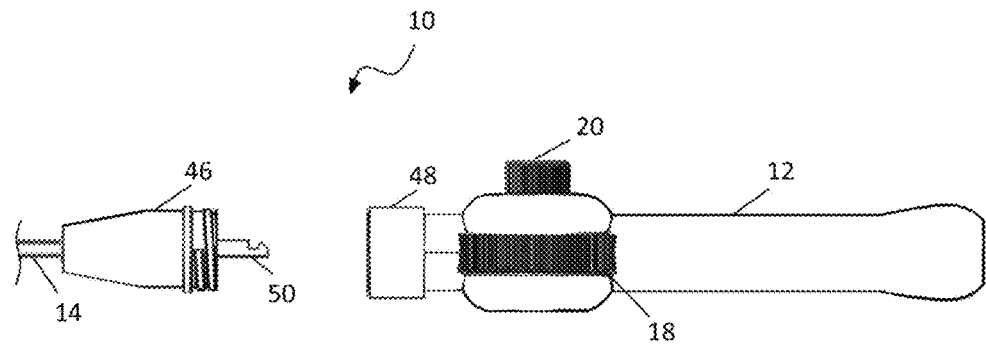
FIG. 3 is a partial schematic view of the reusable handle and the disposable catheter body in a detached configuration, according to one embodiment.

As discussed above, disposable catheter body 14 may be attached to handle 12 as shown in FIG. 1 and may be detached as shown in FIG. 3. In this embodiment, the proximal end of catheter body 14 has a coupling in the form of fitting 46 with external threads that is configured to mate with threaded housing 48 that is rotatably mounted to handle 12 and features complementary internal threads. The tapered profile of fitting 46 also provides a strain relief function by creating a more gradual transition between the rigid handle 12 and the more flexible catheter body 14. In other embodiments, any suitable connection mechanism may be employed, including snaps, latches, bayonet locks, Luer hubs or others. Each puller wire 30 is secured to interconnects 50 (only one visible in this view.) For the sake of clarity, the couplings associated with lead and thermocouple wires 34, sensor cables 38 and irrigation tubing 42 are not shown, but any suitable fluidic or electrical connector system may be employed as desired. For example, edge connectors provided in fitting 46 and threaded housing may be used to couple electrode lead and thermocouple wires 34 and/or sensor cables 38 with PCB 25, In other embodiments, any suitable releasable attachment between handle 12 and catheter body 14 may be employed, such as a snap fit connection, a pneumatic push-in connection or the like.

Figure 4:
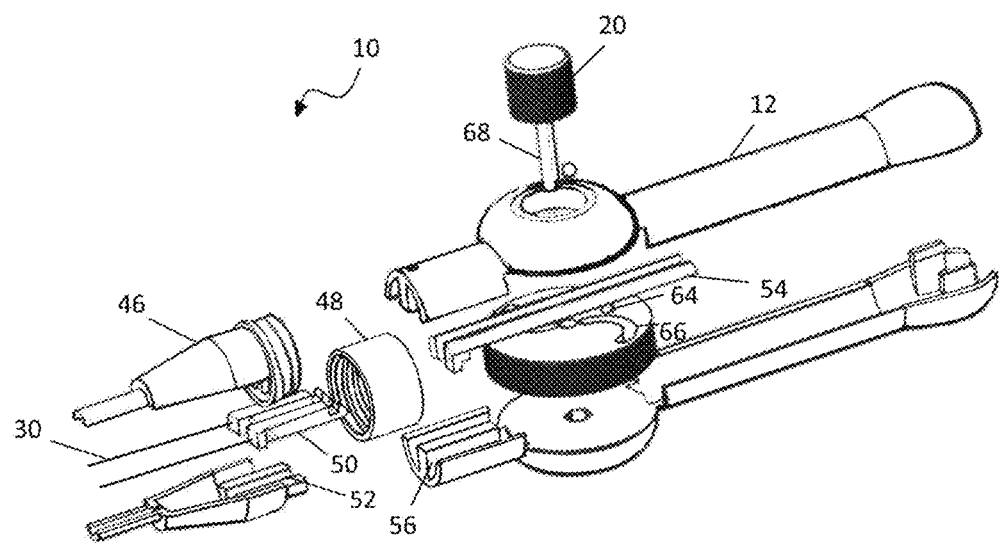
FIG. 4 is an exploded view of the reusable handle and the disposable catheter body in the detached configuration of FIG. 2, according to one embodiment.
Figure 5:
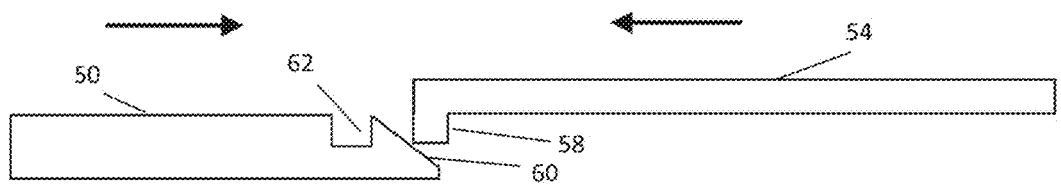
FIGS. 5-7 schematically depict the releasable engagement of a sliding member of the reusable handle with an interconnect of the disposable catheter body, according to one embodiment.
Figure 6:
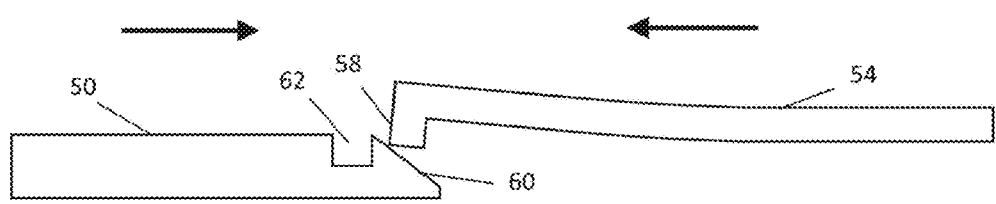
Figure 7:
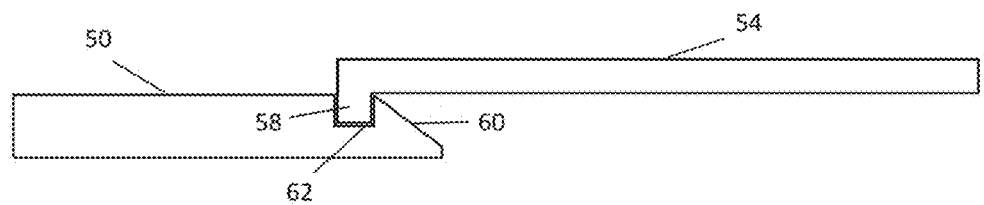

Further details of the actuation mechanism of handle 12 are shown in the exploded view of FIG. 4. As depicted, the complementary halves of fitting 46 define internal supports 52 upon which interconnects 50 travel. Sliding member in the form of two racks 54 are deployed within handle 12, longitudinally moving within guides 56 formed by the complementary halves of handle 12 at a distal location and are configured to allow longitudinal movement and restrict off-axis motion of racks 54. Cooperating structures are positioned at the proximal ends of interconnects 50 and at the distal ends of racks to allow a releasable engagement. In this embodiment, the ends have a hook-shaped configuration. Interaction of these elements is schematically depicted in FIGS. 5-7. As handle 12 and catheter body 14 are brought together, the distal end of each rack 54 contacts the proximal end of each interconnect as shown in FIG. 5. In particular, projection 58 of rack 54 engages ramp 60 of interconnect 50. Further relative movement between rack 54 and interconnect 50 causes projection 58 to ride along the surface of ramp 60 as shown in FIG. 6, deflecting rack 54, which may be formed of any sufficiently resilient material. Notably, interconnects 50 are held in position by supports 52 as rack 54 deflects. Finally, a releasable engagement between rack 54 and interconnect 50 is formed when projection 58 is positioned coextensively over recess 62, allowing rack 54 to return to its nominal configuration, with projection 58 fitting within recess 62 as shown in FIG. 7. As will be appreciated, a similar releaseable engagement between rack 54 and interconnect 50 may be achieved in other embodiments by reversing the configuration of the cooperating ends. Projection 58 and recess 62 may be suitably sized to minimize play between rack 54 and interconnect 50. In this engaged configuration, longitudinal motion of rack 54 is transmitted and causes a corresponding longitudinal motion of interconnect 50. Alternatively, other means may be used to releasably attach proximal ends of the puller wires with structures driven by one or more actuators, including a hook and loop connection, a snap fit connection or a magnetic connection, so that interconnect 50 and the sliding member rack 54 engage when handle 12 is attached to catheter body 14. Accordingly, relative longitudinal movement of rack 54 may be transmitted to the deflection member, puller wire 30, in response to manipulation of actuator 18. Interconnect 50 and rack 54 disengage when handle 12 is released from catheter body 14. In embodiments featuring uni-directional deflection, only a single puller wire 30, interconnect 50 and rack 54 may be required. Other embodiments may include additional components as warranted following these principles to achieve deflection in different directions and/or planes.

Returning to FIG. 4, it may be seen that each rack 54 is coupled to actuator 18 by a cylindrical pin 64 that rides within a camming slot 66 formed in actuator 18. Correspondingly, when actuator 18 is turned, the pins 64 travel within slots 66, and due to the constraint of guides 56, movement of racks 54 is generally longitudinal. Further, since racks 54 are attached to interconnects 50 as described above when handle 12 is mated to catheter body 14, the longitudinal movements of racks 54 are translated to longitudinal movement of puller wires 30, as they are secured to interconnects 50. Puller wires 30 may be directly attached to interconnects 50, or may be coupled by a transitional material, such as a flexible cord, to reduce kinking of puller wires 30 when being moved. As will be appreciated, slots 66 may be designed to produce motion of the racks 54 with desired characteristics. For example, slots 66 may be curved about a radius that displaces racks 54 at the same ratio of rotation to movement no matter what degree actuator 18 has already been turned, such as by having the same ratio throughout the range of travel of actuator 18. In other embodiments, slots 66 may be configured to cause different ratios of motion at different degrees of rotation. Further, the diameter of actuator 18 and length of slots 66 may determine the total amount of movement. In this embodiment, manipulation of actuator 18 causes coordinated movement of the puller wires 30, with one being withdrawn and the other advanced.

Figure 8:
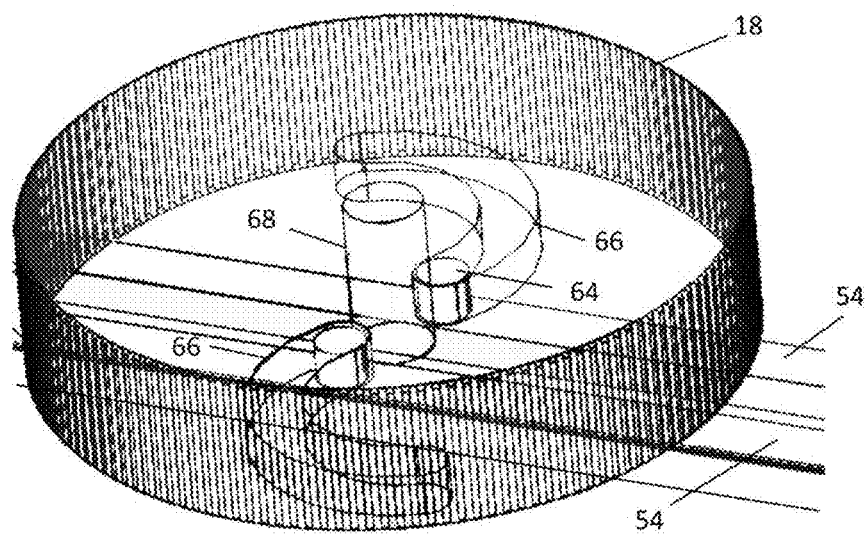
FIG. 8 is a transparent view of the actuator, showing the coupling of sliding members, according to one embodiment.

Additional details regarding the interaction between actuator 18 and racks 54 may be seen in the partially transparent view shown in FIG. 8. This figure depicts actuator 18 at one end of its range of rotational motion, such that clockwise rotation from this position causes pins 64 to travel within slots 66. Since pins 64 project from racks 54, the racks slide longitudinally in response to rotation of actuator 18. Actuator 18 pivots around axle 68, which may be shared with tension knob 20 (not shown in this view.) Although this embodiment relates to a configuration in which actuator 18 is a thumb wheel that is directly manipulated by the user, similar functionality may be achieved by using a rotating member having camming slots that is driven by a separate actuator. Alternatively, actuator 18 may be coupled to racks 54 by one or more gears. As desired, tactile feedback may be provided when actuator 18 is in a neutral position corresponding to no deflection of tip section 16, such as by providing a detent at the appropriate position in the range of travel of actuator 18. Visual or audible indicators may also be employed. In a further aspect, racks 54 may be biased by springs or other mechanisms to return to the neutral position. As such, when tension knob 20 is released, tip section 16 may revert to its non-deflected configuration. Other embodiments may exploit other mechanisms, such as a push button to allow free movement of racks 54 or otherwise allow them to return to their neutral positions.

From the above, it will be appreciated that catheter system 10 represents a cost reduction as compared to conventional disposable catheters, in which the handle is discarded along with the catheter body after use. Since handle 12 is removably attached to catheter body 14, it may be reused following appropriate sterilization and cleaning so that only catheter body 14 need be discarded. The coupling provided by housing 48 and fitting 46 allows for attachment and release of catheter body 14 from handle 12, while simultaneously aligning racks 54 and interconnects 50 to be releasably engaged to transmit forces from actuator 18 to the deflection mechanisms, such as puller wires 30. Further, this coupling may also be used to form connections between wires, leads, cables and/or tubing that may be carried by catheter body 14. As desired, any or all of these components may either pass through handle 12 or connect directly to fitting 46. Further, the modularity of catheter system 10 allows multiple catheter bodies to be used with the same handle, for example to provide different capabilities or functionalities.

Further, although the embodiments discussed above have been in the context of a single disposable catheter body that is releasably attached to a reusable handle, multiple catheter bodies may be employed as desired. For example, two or more tubular shafts may split from a single coupling with the handle. Alternatively, each tubular shaft may connect via separate couplings or backshell connections with the handle. Yet another alternative may involve one or more of the additional catheter bodies connecting to apparatus other than the handle depending on the functionality desired. As will be appreciated, each of the multiple catheter bodies may be employed for different purposes, such as forming an electrical conduit, an independent irrigation lumen or any other suitable function. Depending on the embodiment, such as those incorporating a backhsell connection, the handle may have interior or exterior channels as appropriate to route the catheter body's tubular shafts to the proximal end of the handle.

Figure 9:
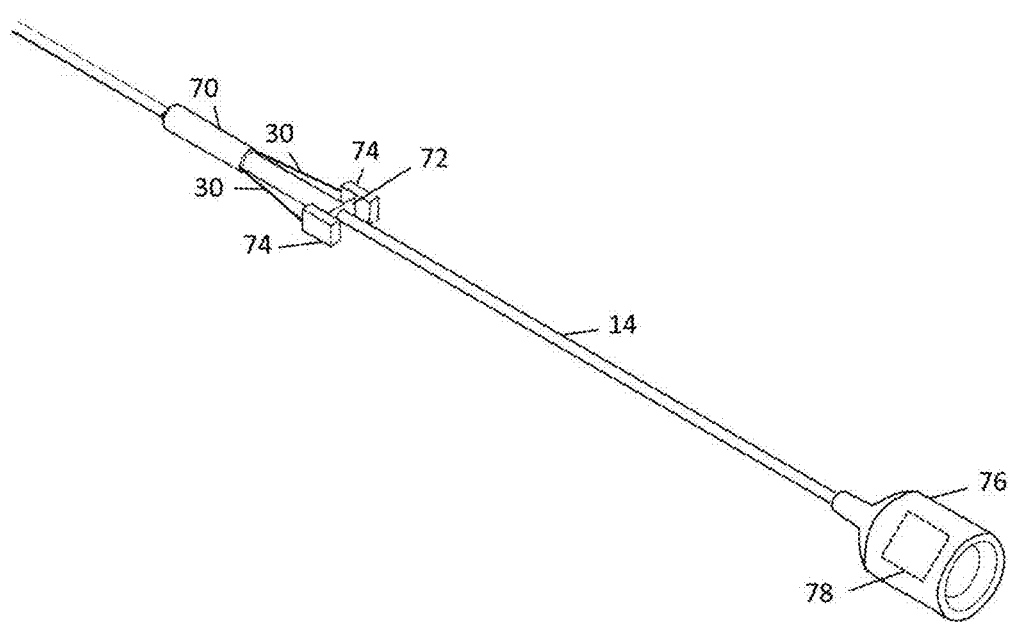
FIG. 9 is a schematic, elevational view of an embodiment of a catheter body having deflection member interconnects stabilized by a frangible support, according to one embodiment.

In another aspect, the puller wires and associated interconnects may be temporarily held in a defined relationship, stabilizing the interconnect(s) to facilitate engagement of the actuator mechanism during connection of the reusable handle. For example, FIG. 9 schematically depicts a disposable catheter body 14 having similar characteristics to those described above. Fitting 70 may have functionality generally equivalent to fitting 46 with regards to facilitating connection to a reusable handle (not shown in this view). Fitting 70 may be overmolded onto catheter body 14 or connected though any other suitable means. In particular, fitting 70 may include frangible support 72 that is configured to retain interconnects 74 in a defined orientation and position with respect to catheter body 14 during attachment of the handle. A backshell 76 may be secured to the catheter body 14 by overmolding or other suitable technique to connect with the handle as desired. While support 72 may have sufficient strength to maintain interconnects 74 in a position to mate with structures equivalent to racks 54, or to be releasably attached through any other suitable interaction, including magnetic, hook and loop, or snap fit as described above, it also may be configured to break upon application of force through an actuator on the handle. As will be appreciated, tailoring the strength of support 72 may be achieved by selecting the appropriate material, such as a polymeric material, by adjusting its thickness or other structural dimension, or both. As desired, a PCB 78 having similar functionality to PCB 25 may be incorporated into the disposable catheter body rather than the handle, such as in backshell 76 as indicated or in any other suitable location. PCB may be used as an alternative to or in conjunction with PCB 25 depending on the embodiment.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable catheter comprising:
   at least one elongated, tubular catheter body having a proximal end and a tip section at a distal end, and a pair of lumens extending therethrough;
   a pair of deflection members, each deflection member slidably disposed within a respective lumen and secured at a distal end to the tip section and terminating in an interconnect at the proximal end;
   a handle releasably attached to the proximal end of the catheter body, the handle comprising at least one actuator; and
   a pair of sliding members associated with the handle and coupled to the actuator, such that manipulation of the actuator causes relative longitudinal movement with respect to the handle, wherein the interconnects and the sliding members engage when the handle is attached to the catheter body so that the relative longitudinal movement of the sliding members is transmitted to the deflection members and wherein the interconnects and the sliding members disengage when the handle is released from the catheter body.

2. The steerable catheter of claim 1, wherein the actuator comprises a rotating member coupled to the sliding member by a pin traveling within a camming slot of the rotating member.

3. The steerable catheter of claim 1, wherein the actuator comprises a rotating member coupled to each sliding member by pins traveling within respective camming slots of the rotating member so that rotation of the actuator in a first direction causes movement of one sliding member in a relatively distal direction and movement of the other sliding member in a relatively proximal direction, while rotation of the actuator in a second direction causes movement of the one sliding member in a relatively proximal direction and movement of the other sliding member in a relatively distal direction.

4. The steerable catheter of claim 1, wherein the camming slot of the actuator is configured to have a radius that displaces the sliding member at a same ratio of rotation to movement over a range of travel of the actuator.

5. The steerable catheter of claim 1, wherein an engagement of the sliding member and the interconnect comprises a projection fitting within a recess.

6. The steerable catheter of claim 5, further comprising a ramp on one of the sliding member and the interconnect to deflect the projection until positioned coextensively with the recess.

7. The steerable catheter of claim 1, wherein the sliding member travels within a guide formed in a distal portion of the handle.

8. The steerable catheter of claim 1, wherein the catheter body is attached to the handle by a threaded housing.

9. The steerable catheter of claim 1, wherein the interconnect is stabilized with respect to the catheter body prior to attachment to the handle by a frangible support.

10. The steerable catheter of claim 9, wherein the frangible support is configured to break following manipulation of the actuator by a user.

11. The steerable catheter of claim 1, further comprising electronic circuitry integrated into at least one of the catheter body and the handle such that the electronic circuitry is in communication with components in the catheter body when the handle is attached to the catheter body.

12. A handle for a steerable catheter comprising:
- a coupling for attaching a proximal end of a catheter body;
- at least one actuator; and
- a pair of sliding members associated with the handle and coupled to the actuator, such that manipulation of the actuator causes relative longitudinal movement with respect to the handle, wherein the catheter body has a pair of deflection members, each deflection member slidably disposed within a respective lumen and secured at a distal end to a tip section and terminating in an interconnect at the proximal end and wherein each sliding member is configured to engage with a corresponding one of the interconnects when the handle is attached to the catheter body so that the relative longitudinal movement of the sliding members is transmitted to the deflection members and wherein the sliding members are configured to disengage from the interconnects when the handle is released from the catheter body.

13. The steerable catheter of claim 12, wherein the actuator comprises a rotating member coupled to the sliding member by a pin traveling within a camming slot of the rotating member.

14. The handle of claim 12, wherein the actuator comprises a rotating member coupled to each sliding member by pins traveling within respective camming slots of the rotating member so that rotation of the actuator in a first direction causes movement of one sliding member in a relatively distal direction and movement of the other sliding member in a relatively proximal direction, while rotation of the actuator in a second direction causes movement of the one sliding member in a relatively proximal direction and movement of the other sliding member in a relatively distal direction.

15. The handle of claim 12, wherein the camming slot of the actuator is configured to have a radius that displaces the sliding member at a same ratio of rotation to movement over a range of travel of the actuator.

16. The handle of claim 12, wherein the sliding member engages the interconnect by a projection fitting within a recess.

17. The handle of claim 12, wherein the sliding member travels within a guide formed in a distal portion of the handle.

18. The handle of claim 12, further comprising electronic circuitry integrated into at least one of the catheter body and the handle such that the electronic circuitry is in communication with components in the catheter body when the handle is attached to the catheter body.

19. An elongated, tubular catheter body comprising a proximal end and a tip section at a distal end, a pair of lumens extending therethrough and a pair of deflection members slidably disposed within a respective lumen, secured at a distal end to the tip section and terminating in an interconnect at the proximal end;

wherein the proximal end of the catheter body is configured to be releasably attached to a handle having at least one sliding member, wherein the interconnect and the sliding member engage when the handle is attached to the catheter body so that the relative longitudinal movement of the sliding member is transmitted to the deflection member and wherein the interconnect and the sliding member disengage when the handle is released from the catheter body.

20. The catheter body of claim 19, wherein the interconnect is stabilized with respect to the catheter body prior to attachment to the handle by a frangible support.

21. The catheter body of claim 19, further comprising electronic circuitry integrated into the catheter body such that the electronic circuitry is in communication with the handle when the handle is attached to the catheter body.

* * * * *